United States Patent [19]

Yoon

[11] 4,254,762
[45] Mar. 10, 1981

[54] SAFETY ENDOSCOPE SYSTEM

[76] Inventor: Inbae Yoon, 2213 Forest Ridge Rd., Timonium, Md. 21903

[21] Appl. No.: 87,648

[22] Filed: Oct. 23, 1979

[51] Int. Cl.³ .............................................. A61B 1/00
[52] U.S. Cl. ........................................ 128/4; 128/754
[58] Field of Search ........................................ 128/4-8, 128/347, 349, 350, 329 R, 348, 753, 754

[56] References Cited

U.S. PATENT DOCUMENTS

| | | | |
|---|---|---|---|
| 2,623,521 | 12/1952 | Shaw | 128/753 X |
| 3,993,079 | 11/1976 | Gatzanondo | 128/347 |
| 4,137,920 | 2/1979 | Bonnet | 128/7 X |
| 4,186,750 | 2/1980 | Patel | 128/748 |

Primary Examiner—Stephen C. Pellegrino
Attorney, Agent, or Firm—Finnegan, Henderson, Farabow, Garrett & Dunner

[57] ABSTRACT

An endoscope with an encircling sleeve slidably mounted in a needle-like trocar, at least the endoscope entering a body cavity under spring bias upon completion of a puncture by the trocar. Preferably, the viewing end of the endoscope is sealed within the sleeve and the trocar and sleeve are detachable from the endoscope and disposable. Impact of the endoscope against the sleeve, as well as the movement of the endoscope, provide signals of completion of the puncture to the surgeon.

19 Claims, 12 Drawing Figures

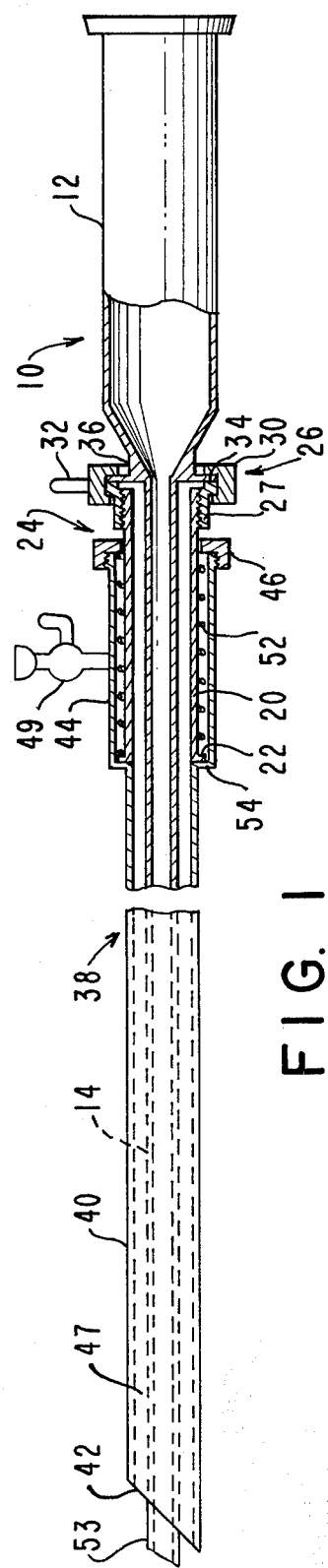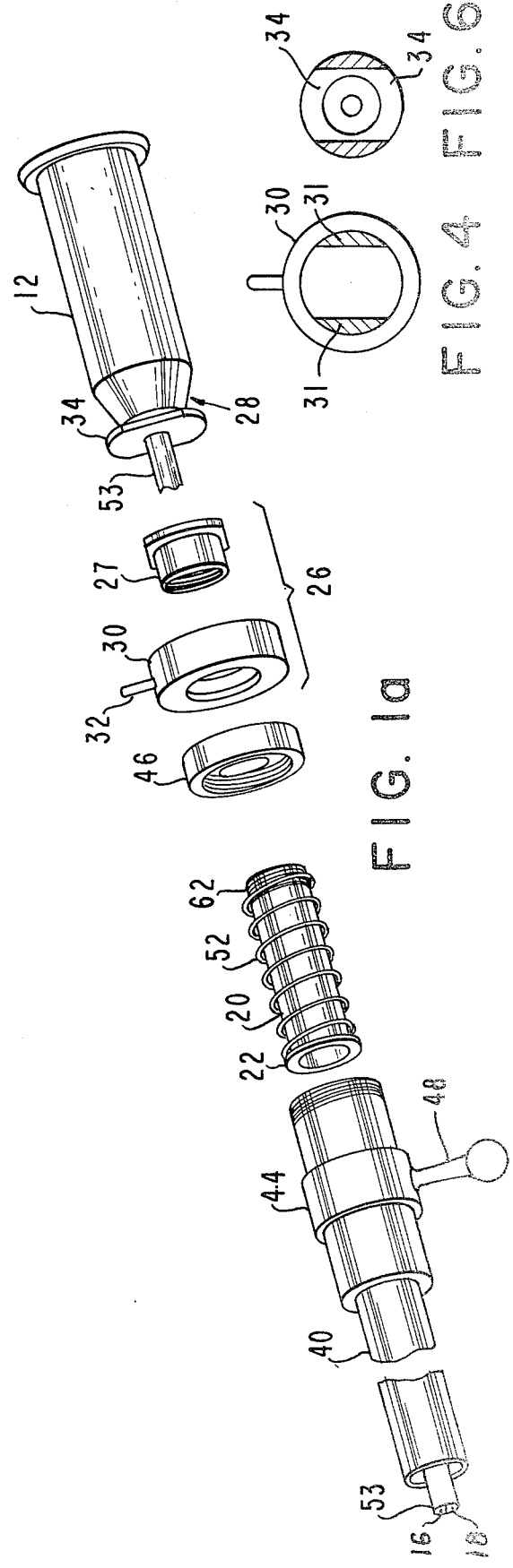

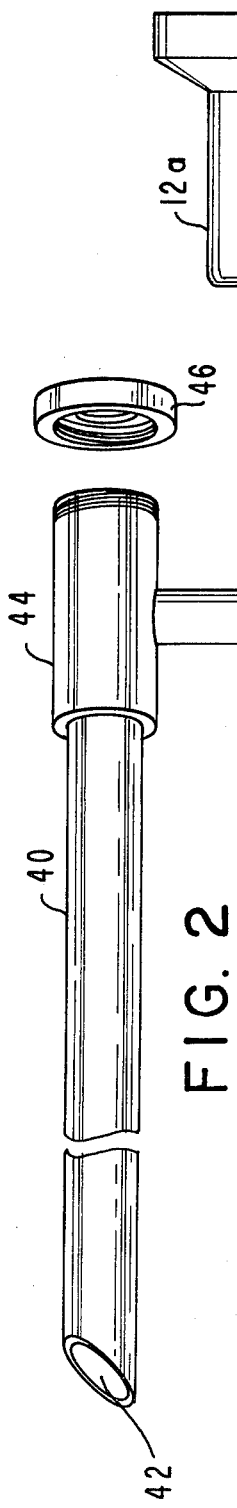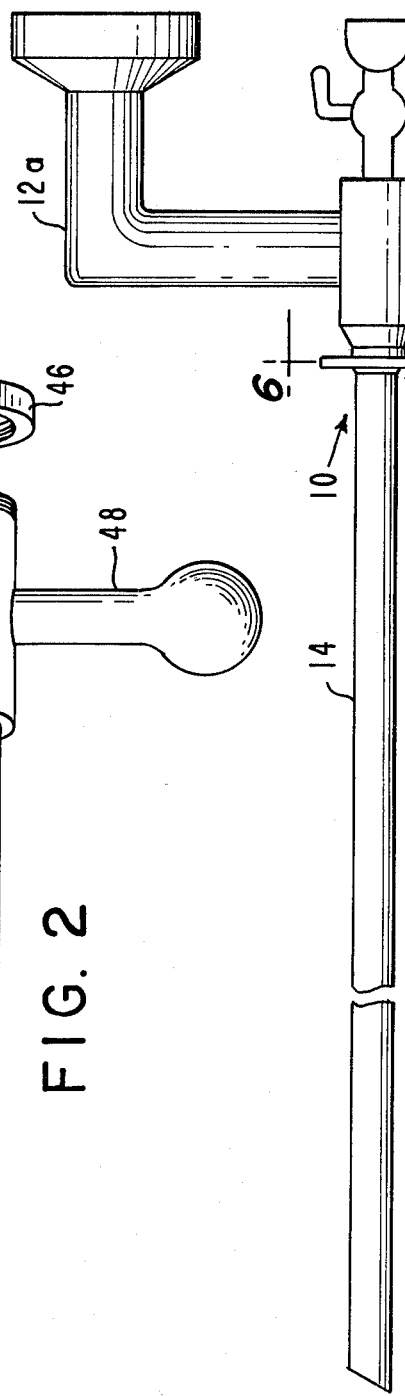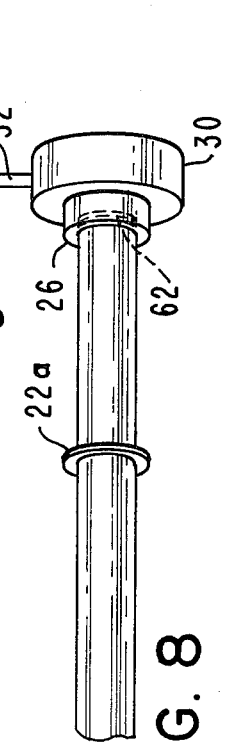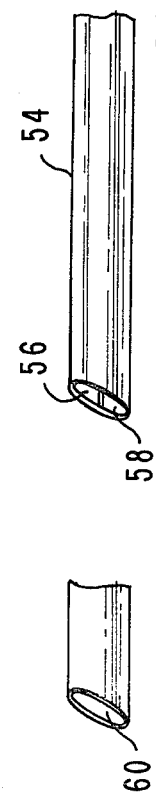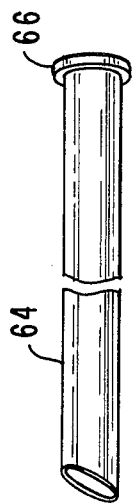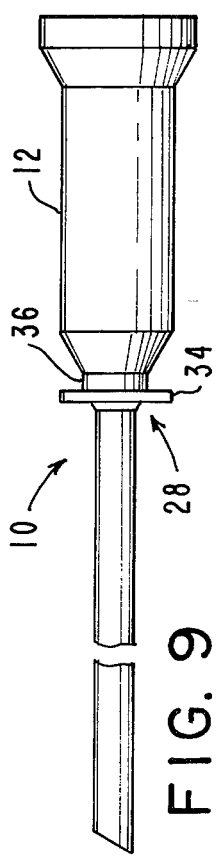

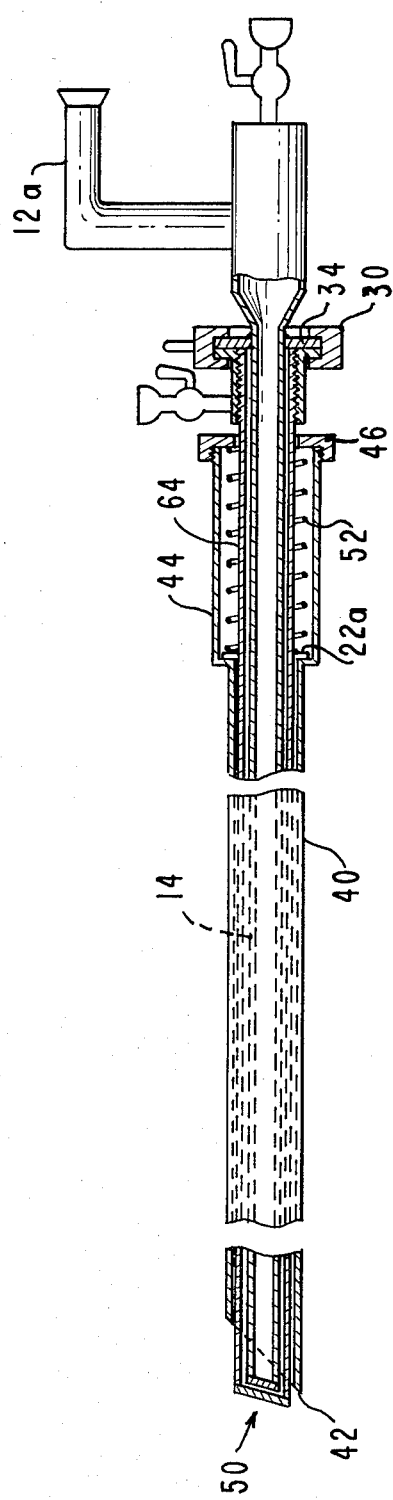
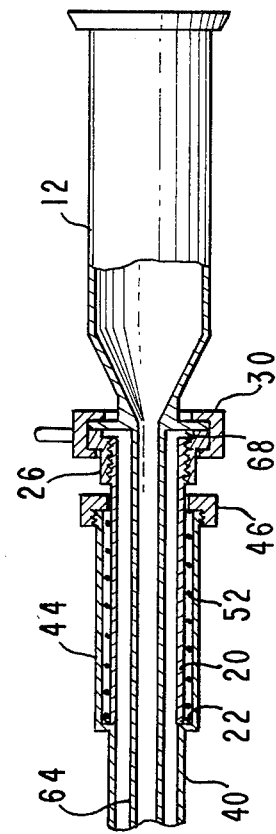
FIG. 7
FIG. 3

SAFETY ENDOSCOPE SYSTEM

The invention relates surgical devices and more particularly to endoscopic devices for use in any endoscopic procedure.

BACKGROUND OF THE INVENTION

In any surgical procedure involving entry into any body cavity, such as puncture of the eyeball or the abdomen, it is of the utmost importance that the surgeon know precisely where his surgical instrument is with respect to the wall of the body cavity. Under conventional procedures, for example, however, the surgeon must proceed blindly during a puncture of the abdominal wall, at least until a pneumoperitoneum has been formed.

For example, in surgical operations involving the puncture of the abdominal wall the surgeon must know immediately when the puncturing instrument, such as a trocar or needle, has entered the abdominal cavity. The peril of puncturing the intestines, or even the aorta, arises as soon as the puncturing instrument enters the abdominal cavity.

To try to mimimize these dangers, instruments and procedures have been developed for giving a signal to the surgeon when the wall of the body cavity has been pierced. One such well-known instrument is the Verres needle. This instrument comprises a needle-like trocar, including a sharpened outside cylinder, and a tubular sensor positioned inside the trocar. The distal end of the sensor normally extends beyond the sharpened point and is spring-biased into this position.

When the Verres needle is being used to puncture the ab- of the body cavity, such as the abdominal wall, the distal end of the senor is pressed back into the trocar by contact with the outer surface of the wall. As soon a the needle-like trocar pierces the wall, however, the sensor is driven outwardly into the cavity by the spring bias. The movement of the sensor signals the surgeon that a puncture has been completed, but the surgeon is completely blind as to the conditions which the piercing instrument and the sensor have encountered.

The distal end of the sensor of the Verres needle is closed by a substantially hemispherical surface. Adjacent this hemispheric closure is an opening for the emission of gas. It is conventional procedure in the puncture of the abdominal wall, after the puncture to allow gas such as carbon dioxide or niturous oxide, under pressure, to flow into the abdomen to lift the abdominal wall away from contents of the abdomen to form a pneumoperitoneum. The danger of inadvertent puncture of an organ in the abdomen is thus reduced.

Perils, however, accompany the use of the Verres needle, which is blind. The abdominal wall, for example, itself is often separated into two wall portions with a cavity therebetween in a condition called preperitoneal emphysema. In this condition, which may not be foreseeable by the surgeon, the distal end of the sensor of the Verres needle enters the preperitoneal cavity and the emitted gas expands the cavity between the inner and outer portions of the abdominal wall. The surgeon then prepares for further procedures, even though the abdominal cavity, itself, has not been entered, unknown to the surgeon.

After the gas has been emitted through the Verres needle, the needle is removed the puncture enlarged by small incisions, and another instrument inserted. The second instrument customarily is a larger solid body trocar for enlarging the puncture made by the Verres needle. Such a solid body trocar includes a solid cylindrical body slidably mounted in a sleeve. The solid cylindrical body has a sharpened point formed by three or four cutaway portions forming a pyramidal point.

The solid body trocar has a relatively large diameter but varying in diameter in accordance with the procedure. This instrument is inserted into the puncture made by the Verres needle blindly by the surgeon. The danger of puncturing an organ in the abdomen, for example, by the large solid body trocar is severe and such a puncture is not always apparent. Of course, if the aorta is punctured, the patient dies quickly.

After the diameter of the puncture has been enlarged by the solid body trocar, including the sleeve, the solid portion of the trocar is removed and an endoscope is inserted through the sleeve to inform the surgeon visually as to the conditions under which further procedures may be advanced.

Under conventional procedures, therefore, the surgeon not only must puncture the body wall blindly, but must first insert the Verres needle, remove the Verres needle, insert the solid body trocar, remove the trocar, and then through the trocar sleeve, insert an endoscope, which conventionally may include an operating channel. It is to be understood that the term "endoscope" is used broadly herein and inludes laparoscopes, peritoneoscopes, and other types of specialized endoscopes.

SUMMARY OF THE INVENTION

It is, therefore, a principal object of the invention to permit the surgon to monitor visually and continuously the puncture of any body cavity.

It is another principal object of the invention to permit the surgeon to proceed immediately to operating procedures, after the puncture of the wall of the body cavity, without having to withdraw the puncturing instrument, or instruments, and to insert a further instrument or instruments.

Additional objects and advantages of the invention will beset forth in part in the description which follows, and in part will be obvious from the description or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the endoscopic device of the invention comprises endoscope means including an eyepiece and an elongated body member, sleeve means encircling at least a portion of the body member, means for releasably attaching the sleeve means to the endoscope means adjacent the junction of the eyepiece and the body member, needle-like trocar means having a hollow cylindrical body with a sharpened distal end for puncturing the wall of a body cavity, the trocar means encircling at least a substantial portion of the body member and the sleeve means, said sleeve means being slidable in said trocar means, and mechanical means mounted in the trocar means for providing a signal at the completion of the puncture of the wall of the body cavity by the trocar means.

By means of this invention, the surgeon is able not only to monitor the operative procedure both visually and continuously, but is able to proceed immediately without change of instrument to further operative proceducres through the operative channel, or channels, of the endoscope.

The accompanying drawings, which are incorporated in and constitute a part of this specification, illustrate at least one embodiment of the invention and, together with the description, serve to explain the principles of the invention.

BRIEF DESCRIPTION OF THE DRAWINGS

FIG. 1 is a schematic drawing, partially in section, of one embodimemt of the endoscopic device of the invention;

FIG. 1a, is an exploded perspective view of a portion of the embodiment of FIG. 1, also including an optional handle.

FIG. 2 is an exploded perspective view of the needle-like trocar of the device of FIG. 1a;

FIG. 3 is a side view, partially broken away, of the cylindrical sleeve element and locking collar of the device of FIG. 1;

FIG. 4 shows an end view of the locking collar of FIG. 3;

FIG. 5 is a schematic drawing of a right angle endoscope useable in the invention;

FIG. 6 is a cross-sectional view taken along the line 6—6 of FIG. 5;

FIG. 7 is a schematic drawings, partially in section, of a second embodiment of the endoscopic device of the invention;

FIG. 8 is a schematic perspective drawing of the cylindrical sleeve and locking collar of FIG. 7; and FIG. 8A depicts a variation in the distal end of the cylindrical sleeve of FIG. 8;

FIG. 9 is a schematic drawing of a rectilinear endoscope useable in the invention; and FIG. 10 is a schematic perspective drawing of an auxiliary sleeve for use in the embodiment of FIG. 1.

DESCRIPTION OF THE PREFERRED EMBODIMENT

Reference will now be made in detail to the present preferred embodiment of the invention, an example of which is illustrated in the accompanying drawings.

A preferred embodiment of the endoscopic device of the invention is shown in FIGS. 1 and 1a. In accordance with the invention, and as shown and described herein, the endoscopic device includes endoscope means including an eyepiece and an elongated body member. As embodied herein, the endoscope means, numbered generally as 10, includes an eyepiece 12 and an elongated cylindrical body member 14.

The eyepiece may include lenses and mirrors, not shown, and means for supplying light, also not shown, all of which are known in the art. The eyepiece may be part of a rectilinear endoscope as shown in FIG. 1 or a right angle endoscope as illustrated in FIGS. 5 and 7.

The elongated body member 14, while keeping its cylindrical form, may have different internal contents according to its utility. It may be, for example, only an optical channel terminating in a piece of transparent material, which may itself be a lens. On the other hand, the elongated body member may be divided into at least two channels, one being an otpical channel 16 and one other an operating channel 18.

In accordance with the invention, the endoscopic device includes sleeve means encircling at least a portion of the elongated body member. As embodied in the endoscopic device of FIGS. 1 and 1a, the sleeve means comprises a sleeve element 20, as also shown in FIG. 3, encirculing a portion of the body memeber 14 and concentric therewith.

The sleeve element 20 includes annular abutment means, shown in FIG. 3 as a ring 22, fixed on the sleeve element for purposes described hereinafter.

Further in accordance with the invention, the endoscopic device includes means for releasably attaching the sleeve means to the endoscope means adjacent the junction of the eyepiece and the body member. As embodied herein, the attaching means, shown generally as 24, includes a locking collar 26 mounted on the sleeve element 20 and a throat structure, numbered generally as 28, on the endoscope means and shown specifically in FIGS. 5 and 6.

The locking collar 26 includes a ring 30 rotatably mounted on a body portion 27, and a projection 32 on the ring for rotating the ring on the body portion in one direction for attaching the sleeve element 20 to the throat 28 of the endoscope means and for rotating the ring in the other direction to release the collar from the throat structure.

The ring 32 has in its inner circumference a restricted opening shown in FIG. 4 for interacting with a complementary structure formed on the throat 28. As illustrated, parallel shoulders 31 have been formed on the inner circumference of the ring 30. A projection 34, shown in FIG. 6, is formed on the throat 28 to slide within the shoulders 32. The throat 28 includes an annular channel 36 (FIG. 5) behind the projection 34, and the thickness of the shoulders 31 is dimensioned for rigidly attaching the sleeve element 20 to the throat 28 by rotation of the ring 30.

It is understood, of course, that the locking collar 24 and the throat 28 are merely one example of apparatus which may be used for attaching the sleeve element 20 to the endoscope means. The sleeve element 20, for example, could be threaded directly onto a complementary surface of the eyepiece 12.

Similarly, the shoulders 31 on the ring 30 and the projection 34 on the throat 28 are merely one example of a structure whereby the rotation of a ring, such as ring 30, can be utilized to lock the sleeve element 20 to the endoscope means.

Further in accordance with the invention, the endoscopic device includes needle-like trocar means having a hollow cylindrical body with a shaprened distal end for puncturing the wall of a body cavity, the trocar means encircling at least a substantial portion of the body member and the sleeve means, the sleeve means being slidable in the trocar means.

As embodied herein, the needle-like troca means, numbered generally as 38, includes a hollow cylindrical body 40 with a sharpened distal end 42 for puncturing the wall of body cavity. The hollow cylindrical body 40 encircles and is concentric with at least a substantial portion of the elongated body member 14 of the endoscope means 10 and the sleeve element 20.

The trocar means 38 includes a portion 44 of enlarged diameter forming its proximal end and an annular cap 46 which is removably attached, as by threads, to the portion 44 to form the proximal end of the portion 44. In assembling the endoscopic device of the invention, as shown in the embodiment of FIG. 1, the sleeve element 20 and the elongated body member 14 of the endoscope means are inserted into the trocar means 38 and are slidable in the annular cap 46, when threaded on the portion 44.

The diameters of the elongated body member 14 of the endoscopic means 10 and the hollow cylindrical body 40 of the trocar means differ enough to provide an annular space 47 for the flow of gas between the body member 14 and the cylindrical body 40 into the abdominal cavity to form the pneumoperitoneum, in case of puncture of the abdominal wall. The gas may enter the annular space 47, for example, through a gas cock 49 formed on the enlarged portion 44 of the trocar means 38.

The trocar means 38 may also include a handle 48, preferably attached to the portion 44 of enlarged diameter of the trocar means. The hollow cylindrical body 40 of the trocar means may be quite small in diameter, such as 1.7 mm., or relatively quite larger, such as 10 mm. It is foreseen that the body 40 of the trocar may be utilized with diameters of 1.7, 2.2, 2.5, 3.0, 5.0, 7.0, 8.0 and 10.0 mm. Other diameters also may be required for efficient use in given surgical procedures. The diameter of the elongated body member 14 of the endoscope means 38 will also vary, as required for optical use and for inclusion of an operating channel or a plurality of operating channels. The handle 48 may be useful and necessary when larger diameters are required and unnecessary when smaller diameters are used.

The sharpened distal end 42 of the hollow body 40 of the trocar means 38 forms a plane preferably at an angle of substantially 45° with the cross section of the body 40. The viewing end, i.e., the distal end, of the elongated body member 14 of the endoscope means preferably forms a cross section of the body member 14 when the diameter of the body 40 of the trocar is small, such as 5 mm. and below. If the diameter of the body 40 of the trocar means is over 5 mm., however, it is preferable that the distal end, i.e., the viewing end, of the elongated body member 14, also form a plane at an angle to the cross section, preferably 35°, such as shown in FIG. 5.

The viewing end 50 of the body member 14 may take any one of a number of forms as circumstances required. It may be open; closed with transparent material; closed with a lens, such as a wide angle 180° lens; or partially covered with transparent material, including a lens for use as an optical channel.

In accordance with the invention, the endoscopic device further includes mechanical means mounted in the trocar means for providing a signal at the completion of the puncture of the wall of the body cavity by the trocar means. As embodied herein, the mechanical means includes a compression spring 52 encircling a portion of the sleeve element 20, and having one end abutting the annular abutment means 22 and the other end abutting the cap 46.

In the embodiment of FIG. 1, the distal end 53 of the elongated body member 14 normally extends beyond the sharpened end 42 of the hollow cylindrical body 40 of the trocar means 38. As previously described, the sleeve element 20 is locked to the endoscope means 10 by the locking collar 24. The endoscope means 10 is therefore biased into its normal postion by the spring 52 acting between the abutment ring 22 of the sleeve element 20 and the cap 46 of the trocar means 38. When pressure is applied to the distal end 53 of the endoscope means, therefore, the elongated body member 14 is pressed back within the cylindrical body 40 of the trocar means against the bias of the spring 52. As the body member 14 is pressed inwardly the sleeve element 20 is carried along by its attachment to the endoscope means 10 and a portion of both the sleeve element 20 and the body member 14 slide through the annular cap 46 compressing the spring 52.

It should also be noted that the eyepiece 12 is part of the endoscope means and is also displaced by pressure on the distal end 53 of the body member 14 of the endoscope means 10. When the sharpened distal end 12 of the cylindrical body 40 pierces the wall of the body cavity, therefore, the endoscope means is released to the bias of the spring 52 and the eyepiece 12 moves away from the eye of the surgeon. In addition, the abutment ring 22 is suddenly driven against an annular shoulder 54 of the enlarged portion 44 of the trocar means 38 giving an audible signal.

The endoscopic device of the invention may use a rectilinear eyepiece 12 and shown in FIG. 1, a right angle eyepiece 12a as shown in FIG. 5, or any other eyepiece known or developed in the art. It is preferred that the eyepiece 12 and the elongated body member 14 be integrated into a single element, but it is not necessary for purpose of the invention.

In the second embodiment of the endoscopic device of the invention, as shown in FIG. 7, and in accordance with the invention, the sleeve means includes a cylindrical sleeve interposed between the cylindrical bodies of the trocar means and the endoscope means, the distal end of the elongated body member of the endoscope means terminating within and adjacent the distal end of the cylindrical sleeve.

As embodied herein, the cylindrical sleeve 54 is elongated extending from the attaching means, such as locking collar 26, to beyond the viewing, i.e., the distal, end of the elongated body member 14 of the endoscope means 10a.

The abutment means 22a, also shown in FIG. 8, is affixed to the sleeve 54 and forms an end position of the spring 52. Spring 52 thereby acts to bias the sleeve 54, with the endoscope means 10a attached thereto through the locking collar 26, outwardly beyond the sharpened tip 42.

The cylindrical sleeve 54 may be sealed at the distal end by transparent material, effectively preventing any intercontact between the endoscope means and the body on which the surgical procedure is being performed. By sealing the cylindrical sleeve 54, only the sleeve and the trocar means have to be absolutely aseptic.

It is possible, for example, that the trocar means, the cylindrical sleeve, the attaching means and the mechanical means, may be fabricated of relatively inexpensive material, such as medically approved plastic, and be disposable after a single use.

It may be desirable that the transparent material be a lens 60 as shown in FIG. 8A forming part of the optical system. In this location it is possible for the lens to be a wide angle lens providing up to 180° of visual field.

On the other hand, the cylindrical sleeve 54 may be at least partially open at the distal end for use with an endoscope means having an optical channel 56 and one or more operating channels 58, as shown in FIG. 8.

If the diameter of the cylindrical body 40 of the trocar means 38 exceeds 5.0 mm., it is preferred that the distal end of the cylindrical sleeve 54 be formed in a plane at an acute angle to the cross section of the sleeve, such as 35°, as shown in FIG. 9. By this means the distal end of the sleeve 54, which is biased against the outer wall of the body cavity during puncture by the trocar means, offers minimum deterrence to the puncture.

FIG. 9 shows a rectilinear endoscope means which may be used with the embodiment of either FIG. 1 or FIG. 7.

The endoscopic device of the invention can be rapidly assembled and dissassembled. In assembly, the spring 52 is positioned on the proximal end of the sleeve element 20, or the cylindrical sleeve 54, with the distal end of the spring abutting the annular abutment 22 or 22a, respectively. The annular cap 46 is then slid over the proximal end of the sleeve means abutting the proximal end of the spring 52. The locking collar 26 is then attached to the proximal end of the sleeve element 20, or the cylindrical sleeve 54, as the case may be, as by threads 62.

The sleeve means, with the spring 52 and annular cap 46 mounted thereon, and retained by the locking collar 26, is inserted into the enlarged portion 44 of the trocar means 38. The cap 46 is then threaded on the enlarged portion 44 of the trocar means 38. The combined trocar means and sleeve means are then attached to the endoscope means by the locking collar, as described previously.

It is sometimes desirable to utilize an auxiliary sleeve as an element of the sleeve means in the embodiment of FIG. 1, interposed between the sleeve element 20 and the elongated body member 14 of the endoscope means 10. Such an auxiliary sleeve, as shown in FIG. 10, may be in any of the forms of the distal end, optical channel and operating channel, or channels, as described above as to sleeve 54.

The auxiliary sleeve 64 is attached to the sleeve element 20 and, through the locking collar 24, to the endoscope means 10. As illustrated in FIG. 3, an annular shoulder 68 may be formed in the body portion of the locking collar 16, so as to be concentric with the auxiliary sleeve 64 when inserted therethrough. A flange 66 on the proximal end of the auxiliary sleeve 64 is seated against the annular shoulder 68. When the locking collar 26 is attached to the endoscope means 10, therefore, the auxiliary sleeve 64 is firmly aligned, as to the elongated body member 14 and the hollow cylindrical body 40. Due to this firm interconnection, the auxiliary sleeve 64 serves the same functions as the sleeves 54 of the embodiment of FIG. 7.

The endoscopic device of the invention permits the surgeon to monitor optically and continuously, not only the puncture of the wall of a body cavity, but also provides immediate assessing of the situation disclosed. Since the endoscopic means provides an operating channel, if desired, the surgeon can continue the surgical procedures without further change of instruments. The amount of time required for the surgical procedure is thus minimized.

It will be apparent to those skilled in the art that various modifications and variations can be made in the endoscopic device of the present invention without departing from the scope or spirit of the invention.

I claim:

1. An endoscopic device comprising:
   endoscope means including an eyepiece and an elongated body member;
   sleeve means encircling at least a portion of said body member;
   means for releasably attaching said sleeve means to said endoscope means adjacent the junction of said eyepiece and said body member;
   needle-like trocar means having a hollow cylindrical body with a sharpened distal end for puncturing the wall of a body cavity, said trocar means encircling at least a substantial portion of said body member and said sleeve means, said sleeve means being slidable in said trocar means; and
   mechanical means mounted in said trocar means interacting between said trocr means and said sleeve means for providing a signal at the completion of the puncture of the wall of the body cavity by said trocar means.

2. The endoscopic device of claim 1 wherein the elongated body member of said endoscope means is cylindrical, slidably mounted in said body of said trocar means and has a viewing end, and wherein said signal means includes means for biasing the viewing end of said cylindrical body of said endoscope means outwardly beyond said sharpened tip.

3. The endoscopic device of claim 1 also incuding an annular space between the cylindrical bodies of said trocar means and said endoscope means, and means of feeding gas into and through said annular space.

4. The endoscopic device of claim 2 wherein said viewing end of the cylindrical body of said endoscope means defines a plane oblique to the right cross section of its cylindrical body.

5. The endoscopic device of claim 4 wherein the sharpened tip defines a plane at about 45° to the right cross section of the cylindrical body of the trocar means and the plane defined by the viewing end is at an angle of about 35° to the right cross section of the cylindrical body of the endoscope means.

6. The endoscopic device of claim 2 wherein said attaching means includes a locking collar mounted on the proximal end of the sleeve means, and wherein said biasing means includes a compression spring interacting between said sleeve means and said locking collar.

7. The endoscopic device of claim 6 wherein said trocar means includes a portion of enlarged diameter forming the proximal end thereof and an annular cap removably attached to the end forming the proximal end of the enlarged diameter portion, said sleeve means being slidable in said annular cap, and wherein said sleeve means includes annular abutment means fixed thereto within and adjacent the distal end of said enlarged portion, said compression spring being wound around the sleeve means and having one end abutting said abutment means and the other end abutting said annular cap.

8. The endoscopic device of claim 7 wherein said sleeve means comprises a sleeve element terminating at said abutment means.

9. The endoscopic device of claim 8 wherein said sleeve means also includes an auxiliary sleeve interposed between said sleeve element and said elongated body member of said endoscope means and extending outwardly beyond the distal end of said elongated body member.

10. The endoscopic device of claim 1 wherein said sleeve means includes a cylindrical sleeve interposed between the cylindrical body of said trocar means and the elongated body member of said endoscope means, the distal end of said elongated body member of said endoscope means terminating within and adjacent the distal end of th cylindrical sleeve.

11. The endoscopic device of claim 10 wherein the said cylindrical sleeve is elongated and said signal means includes means for biasing the distal end of said sleeve outwardly beyond said sharpened tip.

12. The endoscopic device of claim 11 wherein said attaching means includes a locking collar mounted on the proximal end of said cylindrical sleeve and wherein said biasing means includes a compression spring interacting between said cylindrical sleeve and said locking collar.

13. The endoscopic device of claim 12 wherein said trocar means includes a portion of enlarged diameter forming the proximal end thereof and an annular cap removably attached to, and forming the proximal end of, the enlarged portion, said cylindrical sleeve being slidable in said annular cap and wherein said sleeve includes abutment means fixed thereto within and adjacent the distal end of said enlarged portion, said compression spring being wound around the cylindrical sleeve and having one end abutting the abutment means and the other end abutting the annular cap.

14. The endoscopic device of claim 8 or 13, also including handle means attached to said enlarged portion.

15. The endoscopic device of claim 8 or 10 wherein said endoscopic means includes a right angle endoscope.

16. The endoscopic device of claim 10 wherein the distal end of said sleeve is sealed with transparent material.

17. The endoscopic device of claim 16 wherein said transparent material includes a magnifying lens.

18. The endoscopic device of claim 10 wherein the distal end of said sleeve defines a plane at an oblique anlge to the right cross section of the sleeve.

19. The endoscopic device of claim 1 wherein said sleeve means, said attaching means, said trocar means, and said mechanical means are fabricated of medically approved plastic, and thus disposable after a single use.

* * * * *